United States Patent
Suy et al.

(10) Patent No.: US 10,274,450 B2
(45) Date of Patent: Apr. 30, 2019

(54) CAPACITIVE SENSOR

(71) Applicant: ams International AG, Rapperswil (CH)

(72) Inventors: Hilco Suy, Rn Son en Breugel (NL); Zoran Zivkovic, Mn Hertogenbosch (NL); Franciscus Petrus Widdershoven, Hs Eindhoven (NL); Nebojsa Nenadovic, We Wijchen (NL)

(73) Assignee: ams International AG, Rapperswil (CH)

( * ) Notice: Subject to any disclaimer, the term of this patent is extended or adjusted under 35 U.S.C. 154(b) by 52 days.

(21) Appl. No.: 15/505,068

(22) PCT Filed: Aug. 13, 2015

(86) PCT No.: PCT/EP2015/068691
§ 371 (c)(1),
(2) Date: Feb. 17, 2017

(87) PCT Pub. No.: WO2016/026771
PCT Pub. Date: Feb. 25, 2016

(65) Prior Publication Data
US 2017/0261457 A1    Sep. 14, 2017

(30) Foreign Application Priority Data
Aug. 20, 2014 (EP) ..................... 14181602

(51) Int. Cl.
*G01N 27/04* (2006.01)
*G01N 27/22* (2006.01)
(Continued)

(52) U.S. Cl.
CPC ......... *G01N 27/223* (2013.01); *G01N 27/227* (2013.01); *G01N 33/0031* (2013.01);
(Continued)

(58) Field of Classification Search
CPC ........ G01N 27/04; G01N 27/22; G01N 27/26; H01L 21/00; H01L 21/02; H01L 21/20; H01L 23/52; G01R 27/26
See application file for complete search history.

(56) References Cited

U.S. PATENT DOCUMENTS

| | | |
|---|---|---|
| 8,633,047 B2 * | 1/2014 | Hummel et al. ........ H01L 21/00 438/48 |
| 2004/0080325 A1 | 4/2004 | Ogura |

(Continued)

FOREIGN PATENT DOCUMENTS

| | | |
|---|---|---|
| CN | 103487474 A | 1/2014 |
| EP | 1607739 A1 | 12/2005 |

(Continued)

OTHER PUBLICATIONS

Korean Intellectual Property Office, English translation of Notice of Allowance issued in Korean Application No. 10-2017-7007357, dated Jan. 4, 2019, 2 pages.

*Primary Examiner* — Neel D Shah
(74) *Attorney, Agent, or Firm* — Fish & Richardson P.C.

(57) ABSTRACT

A capacitive environmental sensor and a method for determining the presence of a target substance (e.g. water) using differential capacitive measurements. The sensor includes a semiconductor substrate having a surface. The sensor also includes a plurality of sensor electrodes located on the surface. The electrodes are laterally separated on the surface by intervening spaces. The sensor further includes a sensor layer covering the electrodes. The sensor layer has a permittivity that is sensitive to the presence of the target substance. The surface of the substrate, in a space separating at least one pair of electrodes, includes a recess. The surface of the substrate, in a space separating at least one pair of electrodes, does not include a recess. The sensor may be (Continued)

provided in a Radio Frequency Identification (RFID) tag. The sensor may be provided in a smart building.

14 Claims, 9 Drawing Sheets

(51) Int. Cl.
*G01N 27/26* (2006.01)
*H01L 21/00* (2006.01)
*H01L 21/02* (2006.01)
*H01L 21/20* (2006.01)
*H01L 23/52* (2006.01)
*G01R 27/26* (2006.01)
*G01N 33/00* (2006.01)
*H01L 49/02* (2006.01)

(52) U.S. Cl.
CPC ......... *G01N 33/0059* (2013.01); *H01L 28/00* (2013.01); *H01L 28/40* (2013.01); *G01N 33/004* (2013.01); *G01N 33/0047* (2013.01)

(56) References Cited

U.S. PATENT DOCUMENTS

| | | |
|---|---|---|
| 2004/0155751 A1 | 8/2004 | Benzel et al. |
| 2014/0026642 A1 | 1/2014 | O'Connell |
| 2015/0068302 A1* | 3/2015 | Koo et al. ............. G01N 27/22 73/335.04 |

FOREIGN PATENT DOCUMENTS

| | | |
|---|---|---|
| EP | 2565635 A1 | 3/2013 |
| JP | S57148242 A | 9/1982 |
| JP | H0257956 A | 2/1990 |
| JP | 2003028824 A | 1/2003 |
| JP | 2003532080 A | 10/2003 |
| JP | 2004061305 A | 2/2004 |
| JP | 2006058084 A | 3/2006 |
| JP | 2008268169 A | 11/2008 |
| JP | 2012247223 A | 12/2012 |
| JP | 2013190286 A | 9/2013 |
| JP | 2014041034 A | 3/2014 |
| WO | 200231481 A2 | 4/2002 |
| WO | 2009066992 A2 | 5/2009 |
| WO | WO-2012148254 A1 | 11/2012 |

* cited by examiner

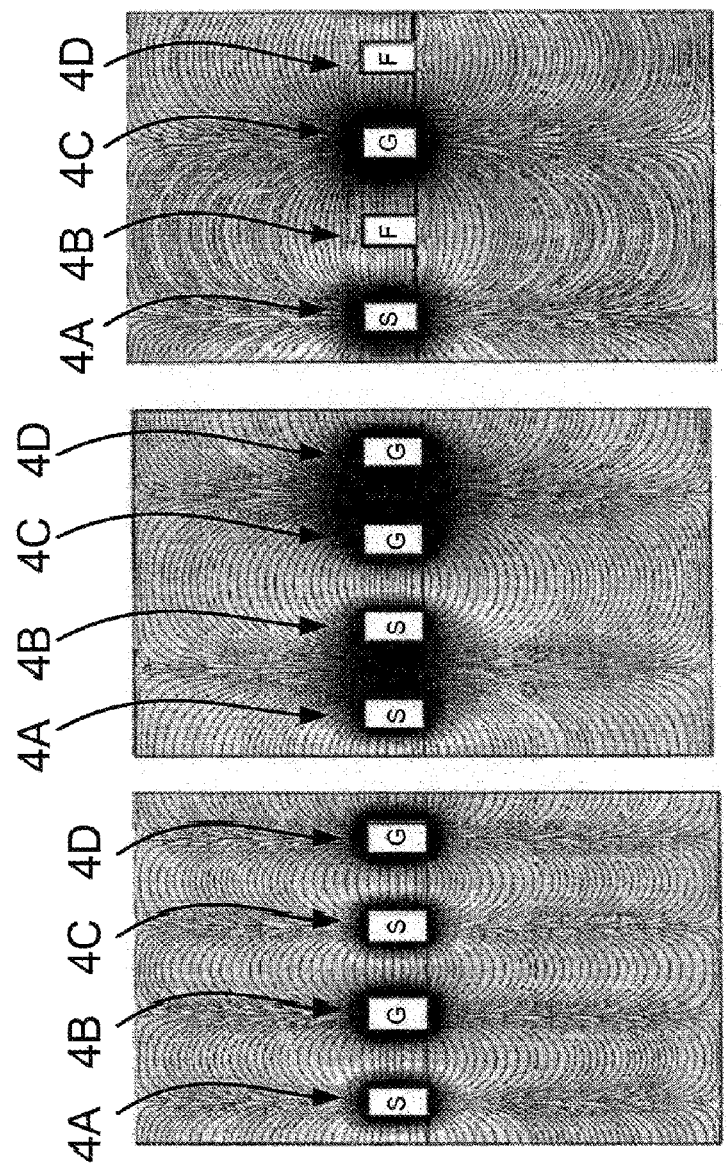

CAPACITIVE SENSOR

FIELD OF THE INVENTION

This invention relates to a capacitive environmental sensor and to a Radio Frequency Identification (RFID) tag or smart building including the sensor. This invention also relates to a method for determining the presence of a target substance using differential capacitive measurements.

BACKGROUND OF THE INVENTION

A known kind of capacitive environmental sensor is shown in FIG. 1. The sensor includes a plurality of electrodes 4 provided on the surface of a semiconductor substrate 2. Oftentimes, the electrodes 4 are provided as a series of interdigitated fingers. A sensor layer 6 covers the electrodes. The sensor layer has a permittivity $\varepsilon$ that is sensitive to the presence of a target substance such as moisture or a gas. Measuring the capacitance of the electrodes can determine the presence of the target substance, since the capacitance of the electrodes is governed at least in part by the permittivity of the sensor layer 6. Depending on the sensitivity of the sensor, an assessment may also be made as to the concentration of the target substance. Typically, the capacitance of the electrode 4 is proportional to the amount of the target substance that enters the sensor layer 6.

Sensors of this kind can suffer from drift. Drift can result from a number of different factors, for example:
- changes in the permittivity of the substrate 2 (e.g. caused by water uptake), which can also contribute to the capacitance of the electrodes 4;
- the presence of substances in the sensor layer other than the target substance (referred to herein a interferents), which can affect the permittivity of the sensor layer and thus affect the capacitance of the electrodes;
- phase transitions or chemical reactions associated with the interferents—these are most likely to occur at an interface between electrodes 4 and the sensor layer 6 ("Water at polymer interfaces", B. D. Vogt, University of Akron, Summer school 2012) and lead to the build-up of an interface layer 8 which can again affect the capacitance of the electrodes 4.

A strategy that has been developed to cope with sensor drift involves making differential measurements of capacitance. For instance the capacitances of the electrodes may be compared to the capacitance of a neighbouring set of electrodes covered by a sensor layer that is not sensitive to the target substance. However, in most cases, process and IC size limitations prevent the use of different functional layers on the same die, whereas multi-chip implementations may not be viable due to the variability in the drift between the different chips. Furthermore, for certain target substances, it may not be possible to identify an appropriate pair of sensor layers.

An alternative approach, described in EP 1607739 A1, involves making differential measurements in a sensor having a single sensor layer and multiple layers of electrodes which may be switched to have different electrical configurations in which separate measurements of capacitance are made. The change in electrical configuration changes the field line distribution within the sensor. This solution suffers however from the relatively complicated layout of the electrodes (in particular the need to provide electrodes in different layers), which can increase manufacturing costs and constrain design freedom in other parts of the substrate.

U.S. Pat. No. 8,633,047 B2 describes a sensor chip comprising a substrate. A plurality of electrode elements is arranged at a first level on the substrate with at least one gap between neighbouring electrode elements. A metal structure is arranged at a second level on the substrate, wherein the second level is different from the first level. The metal structure at least extends over an area of the second level that is defined by a projection of the at least one gap towards the second level.

EP 1607739 A1 does describe an example having a single level of electrodes. However, as will be explained herein, known solutions having a single level of electrodes are generally ineffective, as they suffer from a lack of sensitivity to the target substance.

SUMMARY OF THE INVENTION

Aspects of the proposed concept are set out in the accompanying independent and dependent claims. Combinations of features from the dependent claims may be combined with features of the independent claims as appropriate and not merely as explicitly set out in the claims.

According to an aspect of the proposed concept, there is provided a capacitive environmental sensor. The sensor includes a semiconductor substrate having a surface. The sensor also includes a plurality of sensor electrodes located on the surface. The electrodes are laterally separated on the surface by intervening spaces. The sensor further includes a sensor layer covering the electrodes. The sensor layer has a permittivity that is sensitive to the presence of a target substance. The surface of the substrate, in a space separating at least one pair of electrodes, includes a recess. The surface of the substrate, in a space separating at least one pair of electrodes, does not include a recess.

By providing a recess in the surface of the substrate, in some but not in all of the spaces between the electrodes, a degree of asymmetry may be introduced into the sensor. This may allow differential capacitive measurements to be made that reduce or remove sensitivity of the sensor to a factor or factors other than the presence of the target substance, while retaining sensitivity to the target substance itself. The factors other than the presence of the target substance may, for example, include changes in the permittivity of the substrate, and/or the presence of an interface layer at an interface between the electrodes and the sensor layer.

In some examples the substrate, in at least one space separating a pair of electrodes that does not include a recess, may extend upwards to at least partially fill the space.

The spaces in which the surface of the substrate includes a recess may, in some examples, alternate in a periodic sequence with the spaces in which the surface of the substrate does not include a recess. The alternation of the recessed and non-recessed spaces in a periodic sequence can enhance the ability of the sensor to remove sensitivity to factors other than the presence of the target substance, particularly where multiple repetitions of the sequence are present.

Various examples of periodic sequences are envisaged. For instance, the periodic sequence may be of the form 'XYXYX', where 'X' denotes a space that includes a recess and where 'Y' denotes a space that does not include a recess. Thus in this example, a recess is provided at every second spacing. In another example, the periodic sequence may be of the form 'XYYXYYX'. Thus in this example, a recess is provided at every third spacing. Where the substrate, in a space separating at least one pair of electrodes, extends upwards to at least partially fill the space between the electrodes as noted above (denoted here by 'Z'), the following periodic sequences are also envisaged: 'XZXZX'; 'XZZXZZX'.

As used herein, the term "electrical configuration" is used to refer to the potentials applied to each electrode during a measurement of capacitance. For instance, for making a capacitive measurement, some of the electrodes may be held at ground, some of the electrodes may have a potential applied to them, and some of the electrodes may be left floating.

In one embodiment, the electrodes may include a plurality of separate groups of electrodes arranged on the substrate, each group having a different electrical configuration, for making differential capacitive measurements between each group. In such an example, a differential capacitive measurement can include comparing the capacitance measured by a first group of electrodes with the capacitance measured by a second and/or third group of electrodes, where the groups of electrodes are provided in different areas of the substrate. The different areas of the substrate may be adjacent. In this example, the electrical configurations of the electrodes may be fixed.

In another embodiment, the same set of electrodes may be used to make the differential capacitive measurement. For instance, the electrodes may be switchable between a plurality of different electrical configurations. The switching may be controlled using a microcontroller.

In one embodiment, sensitivity to a factor other than the presence of the target substance may be reduced or removed by comparing measurements of capacitance between two different electrode configurations. This can involve:
  making a first measurement of capacitance of at least some of the electrodes in a first electrical configuration;
  making a second measurement of capacitance of at least some of the electrodes in a second electrical configuration;
  applying a scaling factor to the second measurement to compensate for sensitivity of the sensor to a factor other than the presence of the target substance, and
  determining the presence of the target substance by evaluating the difference between the first measurement and the second measurement.

In some examples, this can be extended to reduce or remove sensitivity to more than one factor other than the presence of the target substance. A third electrical configuration may generally be required in such examples. This may involve:
  making a third measurement of capacitance of at least some of the electrodes in a third electrical configuration;
  applying a scaling factor to the third measurement to compensate for sensitivity of the sensor to a factor other than the presence of the target substance, and
  determining the presence of the target substance by evaluating the differences between the first, second and third measurements.

The scaling factor(s) applied to the second and/or third measurements can reduce or remove sensitivity to the factor(s) other than the presence of the target substance in a manner that retains sensitivity to the target substance itself. As explained herein, the value of scaling factor(s) to be applied may be determined according to the configuration of the recesses (e.g. their depths) in the surface of the substrate.

It is envisaged that the number of measurements made may generally exceed the number of factors other than the presence of the target substance to be accounted for. For instance, the capacitive environmental sensor may be operable to determine the presence of the target substance by: making a plurality of measurements of capacitance of at least some of the electrodes in respective, different, electrode configurations; applying a scaling factor to at least some of the measurements to compensate for sensitivity of the sensor to factors other than the presence of the target substance, and determining the presence of the target substance by evaluating the differences between the measurements. The number of measurements of capacitance made is at least two more than the number of factors other than the presence of the target substance compensated. By making more measurements than are strictly required for compensating for factors other than the presence of the target substance, the accuracy of the measurements for determining the presence of the target substance may be increased.

As used herein, the term "substrate" is used to refer to a semiconductor substrate that may include a plurality of layers (e.g. layers of semiconductor materials, dielectric, metal levels, passivation layers and so forth. The layer may be provided on an underlying semiconductor substrate (e.g. comprising silicon). The electrodes may be located on a surface of one of the plurality of layers. In one example, the electrodes are provided on a passivation layer (e.g. the final passivation layer), and may be applied to the passivation layer during back-end processing in one or more metallization steps.

It is also envisaged that the electrodes may be provided directly on the surface of a monolithic substrate without intervening layers.

The target substance may, for example, be water, $CO_2$ or a volatile organic compound (VOC). Applications of the proposed concept are envisaged for gas/moisture sensing (e.g. in a smart building or greenhouse). Automotive applications, identification applications and use in biosensors are further envisaged.

According to another aspect of the proposed concept, there is provided a Radio Frequency Identification (RFID) tag including a capacitive environmental sensor of the kind described above.

According to a further aspect of the proposed concept, there is provided a smart building including a capacitive environmental sensor of the kind described above.

According to another aspect of the proposed concept, there is provided a method for determining the presence of a target substance using differential capacitive measurements. The method includes providing a capacitive environmental sensor of the kind described above. The method also includes making a first measurement of capacitance of at least some of the electrodes in a first electrical configuration. The method further includes making a second measurement of capacitance of at least some of the electrodes in a second electrical configuration. The method also includes applying a scaling factor to the second measurement to compensate for sensitivity of the sensor to a factor other than the presence of the target substance. The method further includes determining the presence of the target substance by evaluating the difference between the first measurement and the second measurement.

BRIEF DESCRIPTION OF THE DRAWINGS

Embodiments of the proposed concept will be described hereinafter, by way of example only, with reference to the accompanying drawings in which like reference signs relate to like elements and in which:

FIGS. 4A to 4C show the electrical field line distributions for the electrical configurations shown in FIGS. 3A to 3C, respectively;

DETAILED DESCRIPTION

Embodiments of the proposed concept are described in the following with reference to the accompanying drawings.

Embodiments of the proposed concept can provide a capacitive environmental sensor that includes a semiconductor substrate with a plurality of sensor electrodes located on a surface thereof. As described above, the electrodes are separated on the surface by intervening spaces. Some, but not all, of the spaces include a recess in the surface of the substrate. The presence of recesses in the surface of the substrate, where the recesses are located in the spaces between some, but not all of the electrodes, can allow an asymmetry to be introduced into the layout of the sensor that can allow differential measurements to be made that can reduce or remove sensitivity to factors other than the presence of a target substance, while retaining sensitivity to the target substance itself. The factors other than the presence of the target substance can include, for example, changes in the permittivity of the semiconductor substrate (e.g. due to the absorption of moisture) and/or the existence of an interface layer at an interface between the electrodes and a sensor layer that covers the electrodes.

Figure 1:
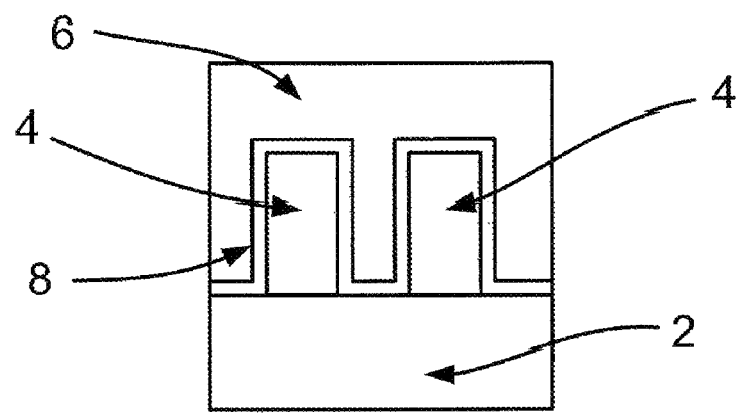
FIG. 1 shows a capacitive sensor including a plurality of sensor electrodes located on the surface of a semiconductor substrate.
Figure 2:
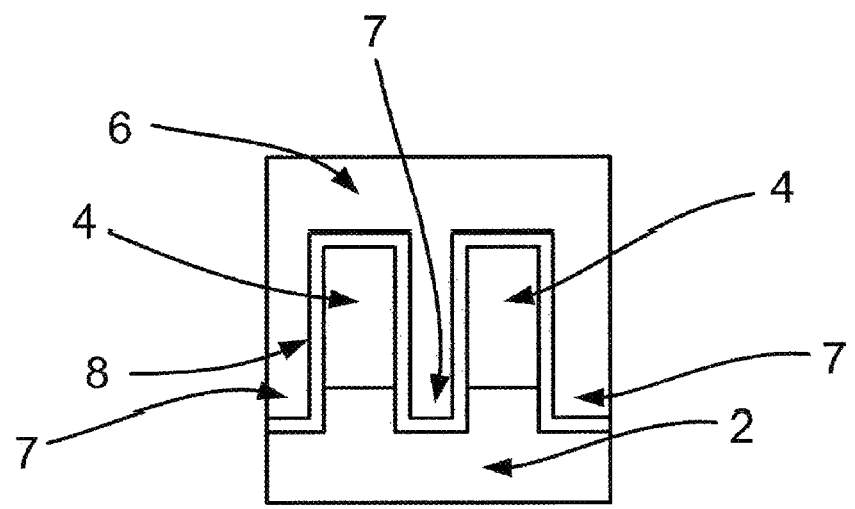
FIG. 2 shows a capacitive sensor including a plurality of sensor electrodes located on the surface of a semiconductor substrate, where the surface of the substrate, in the spaces separating each electrode, includes a recess.

FIG. 2 shows an example of a capacitive environmental sensor. The sensor includes a substrate 2. The sensor also includes a plurality of electrodes 4 which are located on a surface of the substrate 2. The sensor also includes a sensor layer 6. The sensor layer 6 has a permittivity that is sensitive to the presence of a target substance. As noted above, an interface layer comprising substances other than the target substance can build up at an interface between the electrodes 4 and the sensor layer 6. In FIG. 2, this interface layer is denoted using reference numeral 8.

It has been suggested that by placing a recess in the substrate between the electrodes 4, sensitivity to factors other than the presence of the target substance can be mitigated. These recesses are denoted using reference numeral 7 in FIG. 2. As can be seen from FIG. 2, a recess is placed between every pair of electrodes. In this regard, it will be appreciated that FIG. 2 is a simplified diagram showing only two electrodes 4 whereas, as a matter of practice, normally more than two electrodes may be provided.

Figure 3A:
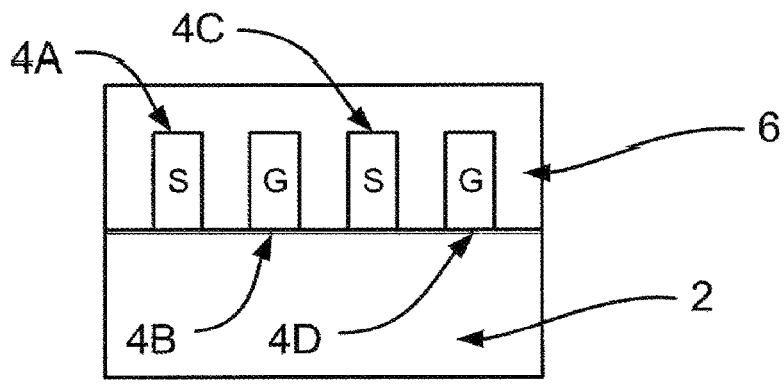
FIGS. 3A to 3C show a number of electrical configurations of the electrodes of a capacitive sensor for performing differential measurements.
Figure 3B:
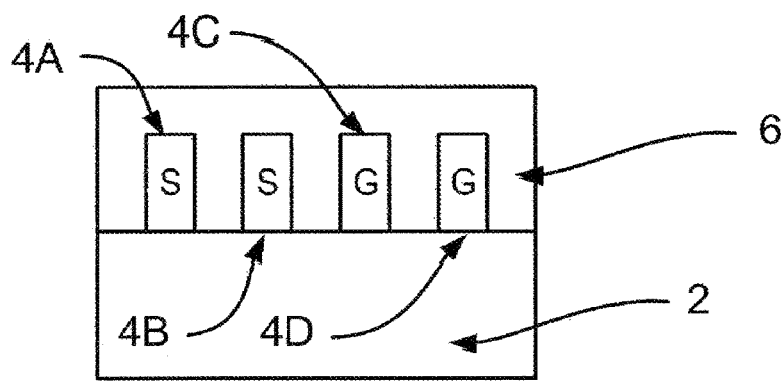
Figure 3C:
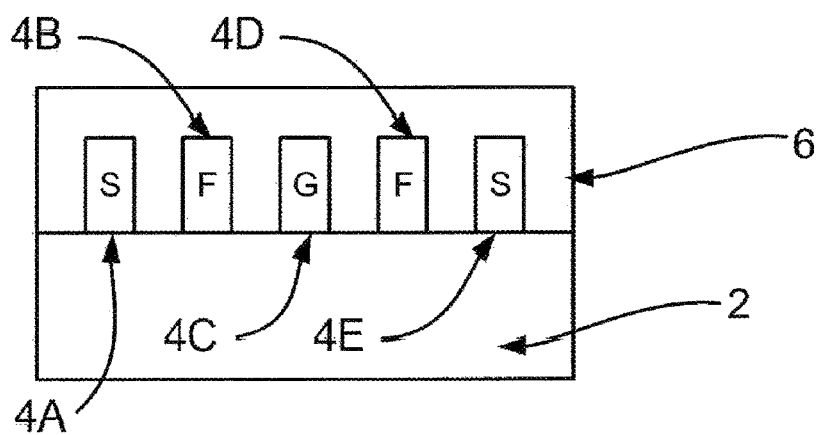

FIGS. 3A to 3C illustrate a number of different electrical configurations for a plurality of electrodes in a sensor of the kind shown in FIG. 2. The term "electrical configuration" is used to refer to the potentials applied to the electrodes during measurements of capacitance.

FIG. 3A shows four electrodes 4A, 4B, 4C, 4D in a configuration that will be referred to herein as the "single spacing" configuration or the "single" configuration. In this configuration, a measurement of the capacitance of the electrodes is made by connecting the electrodes 4B and 4D to ground, while a signal (e.g. a DC potential) is applied to the electrodes 4A, 4C. These signal and ground connections are denoted in the figures by "S" and "G".

FIG. 3B shows an electrical configuration of the electrodes that will be referred to herein as the "double spacing" configuration or the "double" configuration. In the double configuration, to make a measurement of the capacitance, the electrodes 4A and 4B are connected to a signal potential, while the electrodes 4C and 4D are connected to ground. Accordingly, with reference to FIGS. 3A and 3B it will be appreciated that the single configuration includes neighbouring pairs of electrodes that include a first electrode connected to ground and a second electrode connected to a signal, whereby a potential difference appears across the neighbouring electrodes, while the double configuration, includes neighbouring pairs of electrodes that are connected either to a signal potential or to ground.

It is envisaged that in some examples some of the electrodes may be left floating. Floating electrodes are denoted in the figures as "F". The floating electrodes can be located in between the electrodes of a single or double configuration. For instance, FIG. 3C shows an electrical configuration that may be referred to as the "single floating configuration". In this configuration, a set of electrodes 4A, 4C, 4E in the single configuration (c.f. FIG. 3A) are interspersed with floating electrodes 4B, 4D. It is envisaged that other floating configurations may be provided, for instance by interspersing electrodes having a double configuration as shown in FIG. 3B with floating electrodes.

For simplicity, the possible recesses are not shown in FIGS. 3A to 3C.

FIGS. 4A to 4C show the electrical field line distributions produced by the electrical configurations shown in FIGS. 3A to 3C, respectively. It will be appreciated from a comparison of FIGS. 4B and 4C that the field lines produced by the double spacing configuration and the single floating configuration are similar. In the following description, the single spacing configurations such as that shown in FIG. 3A and the double spacing configurations such as that shown in FIG. 3B will be concentrated upon for illustrative purposes. Nevertheless, it is envisaged that electrode configurations including at least some floating electrodes fall within the scope of the claimed concept.

In order to make a differential measurement, a capacitive measurement can first be made with the electrodes having a first electrical configuration (for instance, the single configuration of FIG. 3A) and a second measurement of capacitance can then be made using electrodes having a second electrical configuration (for example, the double configuration shown in FIG. 3B). By comparing these two measurements, it may be possible in principle to factor out contributions from, for example, the presence of an interface layer and/or changes in the permittivity of the substrate.

It is envisaged that differential measurements can be made either by using a single set of electrodes that are switched between a plurality of different electrical configurations, or alternatively by using a plurality of different sets of electrodes that are each hard wired to have different electrical configurations. As will also be described below in more detail, where it is desired to factor out a single factor other than the presence of the target substance, typically only a first and a second electrical configuration may be needed, with a separate measurement of capacitance being taken using each configuration. Where it is desired to reduce or remove sensitivity to two or more factors other than the presence of the target substance, it may generally be necessary to include additional electrode configurations with an additional measurement of capacitance being made at each configuration. In general, the measurements of capacitance made using each electrical configuration can be used to solve simultaneous equations relating to the various factors that affect the measurements of capacitance, thereby allowing the contribution to the measurement associated with the presence of the target substance to be isolated from other factors.

The sensitivity of the electrodes in different electrical configurations can be modelled and simulated. In the following, the results of such modelling are described in respect of electrodes having the single configuration and the double configuration of FIGS. 3A and 3B, respectively.

Firstly, Table 1 shown below shows the sensitivities for the single and double electrode configurations of FIGS. 3A and 3B where the depth of the recesses 7 between each electrode is set to zero.

TABLE 1

Capacitive sensitivities for single and double electrode configurations at zero recess depth.

| Configuration | $\partial C/\partial t_{inter}$ [fF/nm] | $\partial C/\partial \varepsilon_{sub}$ [fF] | $\partial C/\partial \varepsilon_{sens}$ [fF] |
|---|---|---|---|
| Single | 6.73 | 25.0 | 122.3 |
| Double | 3.57 | 20.4 | 70.8 |
| Single - 1.9 * Double | −0.05 | −13.8 | −12.2 |
| Single - 1.2 * Double | 2.45 | 0.52 | 37.3 |

As shown in Table 1, each configuration (i.e. the single configuration and the double configuration) has a certain sensitivity to $\partial C/\partial t$ (where C is the capacitance of the configuration and where t is the thickness of the interface layer 8 which is assumed to be comprised of condensed water ($\varepsilon=80$)), $\partial C/\partial \varepsilon_{sub}$ (where $\varepsilon_{sub}$ is the permittivity of the substrate) and $\partial C/\partial \varepsilon_{sens}$ (where $\varepsilon_{sens}$ is the permittivity of the sensor layer 6).

Comparison of measurements made in the single and double configurations can allow for sensitivity to factors such as the thickness of the interface layer or the permittivity of the substrate to be removed. For instance, by deducting a measurement taken in the double configuration from a measurement taken in a single configuration, where the deducted measurement in the double configuration is first multiplied by a scaling factor (equal to 1.9) it can be seen from Table 1 that sensitivity to the thickness of the interface layer can be substantially reduced or removed ($\partial C/\partial t=−0.05$). The use of a scaling factor equal to 1.9 in this example does not however lead to a complete removal of the sensitivity to the permittivity of the substrate ($\partial C/\partial \varepsilon_{sub}=−13.8$). Moreover, the use of the scaling factor 1.9 has a deleterious effect on the sensitivity of the sensor to the presence of the target substance ($\partial C/\partial \varepsilon_{sens}=−12.2$ compared to a single measurement taken in the single configuration where $\partial C/\partial \varepsilon_{sens}=122.3$ or a single measurement in the double configuration in which $\partial C/\partial \varepsilon_{sens}=70.8$).

Alternatively, a scaling factor of 1.2 may be chosen to substantially reduce or remove sensitivity to the permittivity of the substrate (using a scaling factor of 1.2, it is shown in Table 1 that the value of $\partial C/\partial \varepsilon_{sub}$ becomes 0.52). However, the use of an appropriate scaling factor for reducing or removing sensitivity to the permittivity of the substrate does not substantially reduce or remove sensitivity to the interface layer ($\partial C/\partial t=2.45$) and also leads to a reduction in the sensitivity of the sensor to the presence of the target substance ($\partial C/\partial \varepsilon_{sens}=37.3$).

FIGS. 5 and 6 extend the simulation results of the kind shown in Table 1 by introducing a recess, having a non-zero depth, between each electrode as explained above in relation to FIG. 2.

Figure 5A:
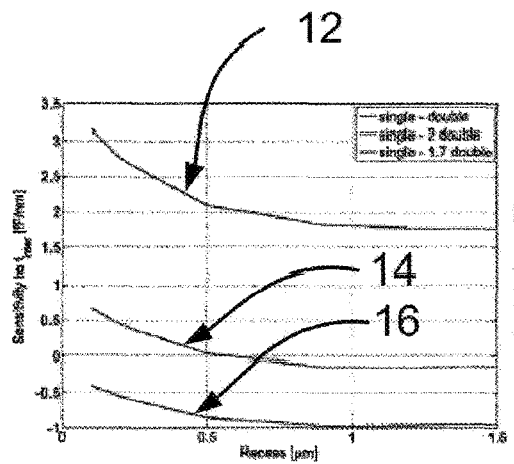
FIGS. 5A and 5B show the effect of varying the depth of a recess in the spaces separating the electrodes.
Figure 5B:
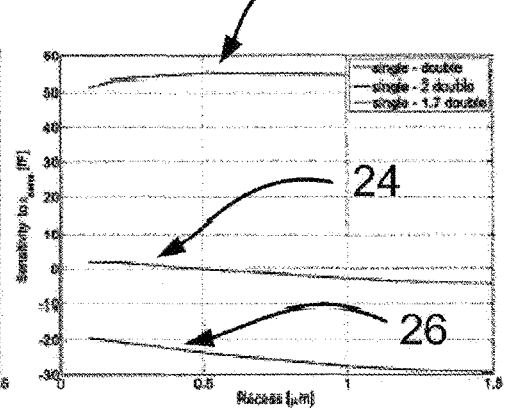

For instance in FIG. 5A, the sensitivity of the sensor to the thickness of the interface layer (t) is shown for a series of differential measurements. As noted above, in this example the differential measurement involves deducting a measurement taken in the double configuration from the measurement taken in the single configuration, with the application of a scaling factor. Similarly, in FIG. 5B the sensitivity of the sensor to the target substance is shown using the same differential measurements and scaling factors used in FIG. 5A. In this way, the effect of various scaling factors can be studied as a function of the depth of the recesses. Details of the various plots shown in FIGS. 5A and 5B are set out in Table 2 below.

TABLE 2

Differential Measurements in FIG. 5.

| FIG. | Reference Numeral | Measurement |
|---|---|---|
| 5A | 12 | Single - 1.0 * Double |
| 5A | 14 | Single - 1.7 * Double |
| 5A | 16 | Single - 2.0 * Double |
| 5B | 22 | Single - 1.0 * Double |
| 5B | 24 | Single - 1.7 * Double |
| 5B | 26 | Single - 2.0 * Double |

For the purposes of this example, assume that the depth of the recesses is chosen to be 0.5 µm. As can be seen from the plot 14 in FIG. 5A, this calls for a scaling factor of 1.7, in order that the sensitivity to the thickness of the interface layer is approximately zero (see plot 14). Turning to FIG. 5B however, at a recess depth of 0.5 µm and a scaling factor of 1.7, plot 24 shows that the sensitivity of the sensor to the presence of the target substance is also approximately zero at this point.

Figure 6A:
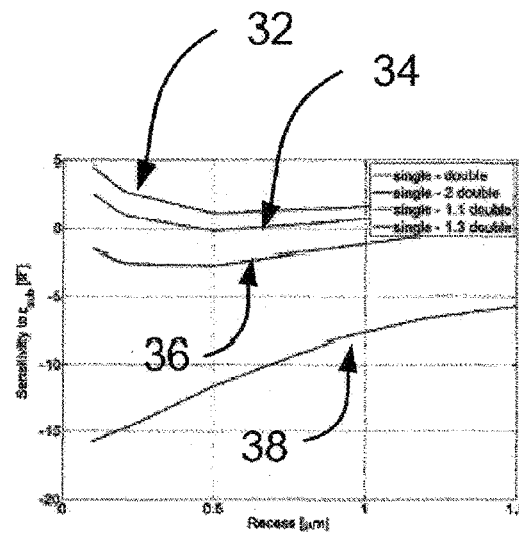
FIGS. 6A and 6B show the effect of varying the depth of a recess in the spaces separating the electrodes.
Figure 6B:
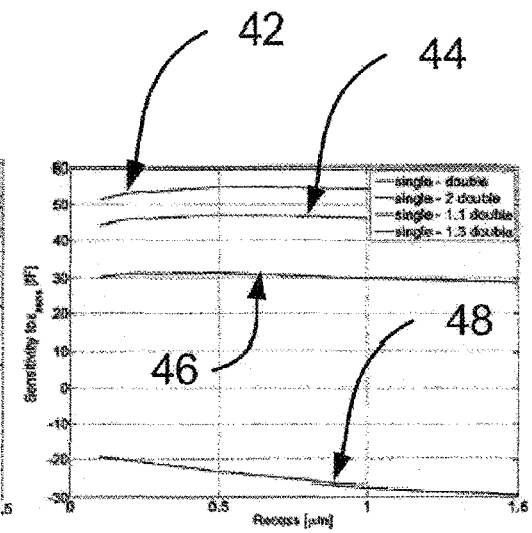

FIGS. 6A and 6B include plots that are summarised below in Table 3.

TABLE 3

Differential Measurements in FIG. 6.

| FIG. | Reference Numeral | Measurement |
|---|---|---|
| 6A | 32 | Single - 1.0 * Double |
| 6A | 34 | Single - 1.1 * Double |
| 6A | 36 | Single - 1.3 * Double |
| 6A | 38 | Single - 2.0 * Double |
| 6B | 42 | Single - 1.0 * Double |
| 6B | 44 | Single - 1.1 * Double |
| 6B | 46 | Single - 1.3 * Double |
| 6B | 48 | Single - 2.0 * Double |

These plots show the sensitivity of the sensor to the permittivity of the substrate (FIG. 6A) and the corresponding sensitivity of the sensor to the presence of the target substance (FIG. 6B), for a number of different scaling factors.

Firstly, in FIG. 6A, it can be seen that at a recess depth of, for example, 0.5 µm, plot 34 illustrates that a scaling factor of 1.1 applied to a differential measurement in which a measurement in the double configuration is deducted from a measurement taken in the single configuration, is suitable for removing sensitivity of the sensor to the permittivity of the substrate. However, as can be seen from FIG. 6B, at a scaling factor of 1.1 and a recess depth of 0.5 µm (see plot 44), the sensitivity of the sensor to the target substance is reduced compared to, for example a simple differential measurement in which a measurement in the double configuration is deducted from a measurement in the single configuration (scaling factor=1.0).

Accordingly, it has been described that by selecting the appropriate recess depth and scaling factor in a differential measurement for a sensor including a plurality of electrodes having different electrical configurations, it is possible to reduce or remove sensitivity of the sensor to factors other than the presence of the target substance. However, it has also been demonstrated that for an arrangement in which a recess is placed between each adjacent pair of electrodes, it is difficult to choose appropriate values for the recess depth and scaling factors that can effectively reduce or remove contributions such as the presence of an interface layer or the permittivity of the substrate without also substantially reducing the sensitivity of the sensor to the target substance itself.

In accordance with embodiments of the proposed concept, it has been realised that by introducing a degree of asymmetry into the layout of the electrodes and recesses, the above noted problem relating to substantial reductions in the sensitivity of the sensor to the presence of the target substance itself can be mitigated.

Figure 7:
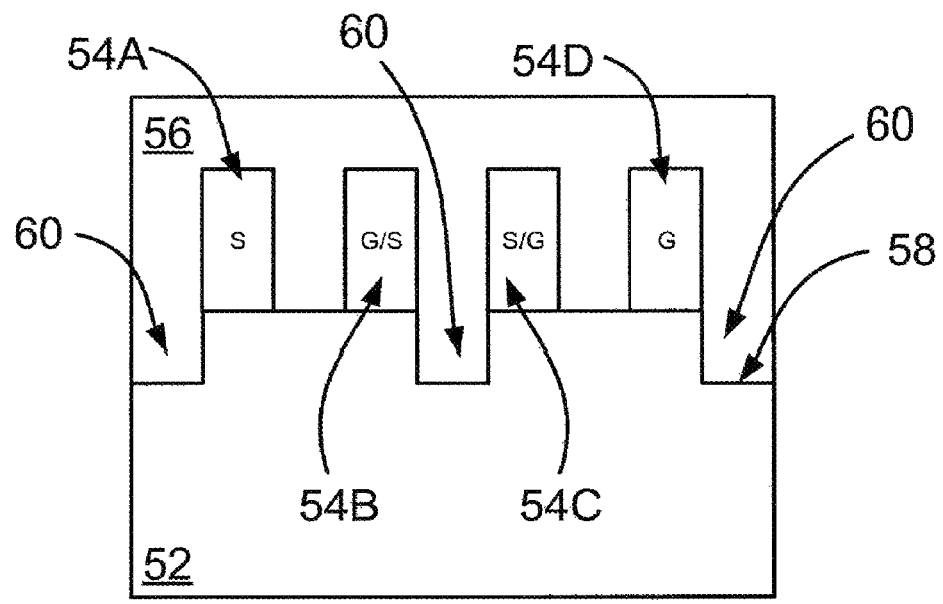
FIG. 7 shows a capacitive environmental sensor according to an embodiment of the proposed concept.

FIG. 7 shows a capacitive environmental sensor in accordance with an embodiment of the proposed concept. The sensor includes a semiconductor substrate 52. The substrate may, for example, comprise silicon. The substrate 52 has a surface 58. The substrate 52 may, in some examples, include a plurality of layers provided on an underlying silicon die. The plurality of layers may for instance include semiconductor layers for forming components such as transistors in the die, one or more metallization layers and one or more dielectric layers separating the metallization layers. The layers can also include one or more passivation layers. The surface 58 in the present example is the surface of an uppermost passivation layer of the substrate. In other examples, it is envisaged that the surface 58 may be the bare surface of a semiconductor die, without any intervening layers.

The sensor includes a plurality of sensor electrodes 54A, 54B, 54C, 54D. The sensor electrodes 54A, 54B, 54C, 54D may be provided as a series of interdigitated fingers as is known in the art. The vertical thickness of the electrodes may be 0.1 µm≤H≤10 µm. The electrodes may comprise any suitable electrically conductive material such as a metal or alloy (e.g. Al, W, Cu), possibly covered by a liner for adhesion purposes in fabrication, and moisture and corrosion barrier purposes during application (e.g. $Ta_2O_5$, Ti, TiN, SiOx or SiN). The liner may typically also cover the surface 58, in addition to the electrodes 54A, 54B, 54C, 54D whereby moisture may be prevented from entering the substrate 52.

The sensor electrodes are located on the surface 58 of the substrate 52. As shown in FIG. 7, the sensor electrodes are laterally separated on the surface 58 by intervening spaces. The lateral width of the spacings may typically be 0.1 µm≤W≤20 µm.

The capacitive environmental sensor also includes a sensor layer 56. The sensor layer 56 covers the electrodes 54A, 54B, 54C, 54D. The sensor layer has a permittivity that is sensitive to the presence of the target substance. The target substance may, for example, comprise water (for example, where the capacitive environmental sensor is a humidity or moisture sensor), $CO_2$ or a volatile organic compound (VOC). The composition of the sensor layer 56 can be selected according to the target substance. For example, in the case of a humidity sensor, the sensor layer 56 may comprise polymers like polyimide, parylene, or PDMS.

The electrodes 54A, 54B, 54C, 54D in this example are switchable between two electrical configurations. In some embodiments, this switching can be controlled by a microcontroller, which may also collect and evaluate the measurements taken for each electrical configuration. As noted above, in an alternative example, it is envisaged that two separate groups of electrodes of the kind shown in FIG. 7 may be placed in different locations on the substrate 52. The different sets or groups of electrodes may be located on completely different parts of the substrate 52 or may in some examples be places adjacent to each other. The first group of electrodes can have a first electrical configuration and the second group of electrodes can have the second electrical configuration for allowing differential measurements to be made between the two groups.

The first electrical configuration in FIG. 7 is a single spacing configuration in which the electrode 54B is switched to ground and the electrode 54C is switched to have a signal applied thereto (typically a DC potential). The electrical configuration in this state is thus "SGSG".

In the second electrical configuration, the electrode 54 is switched to have a signal applied thereto, while the electrode 54C is switched to ground. In this electrical configuration, the electrodes are connected as follows "SSGG", which will be recognised as the double spacing configuration described above.

It will be noted that switching between the single spacing configuration and the double spacing configuration does not, in the present example, involve changing the state of the electrode 54A (which remains connected to "S") or the electrode 54D (which remains connected to "G").

In this embodiment, the surface 58 of the substrate 52 includes a number of recesses 60. The recesses 60 are located in some, but not all, of the spaces between the electrodes 54A, 54B, 54C, 54D. Accordingly, the surface 58 of the substrate 52, in a space separating at least one pair of electrodes in the present example, includes a recess, whereas the surface 58 of the substrate 52, in a space separating at least one pair of electrodes, does not include a recess. This arrangement of the recesses introduces a degree of asymmetry to the layout of the sensor. This asymmetry can, as will be demonstrated below, allow differential measurements to be made in a manner that does not substantially reduce or remove the sensitivity of the sensor to the target substance.

Figure 8:
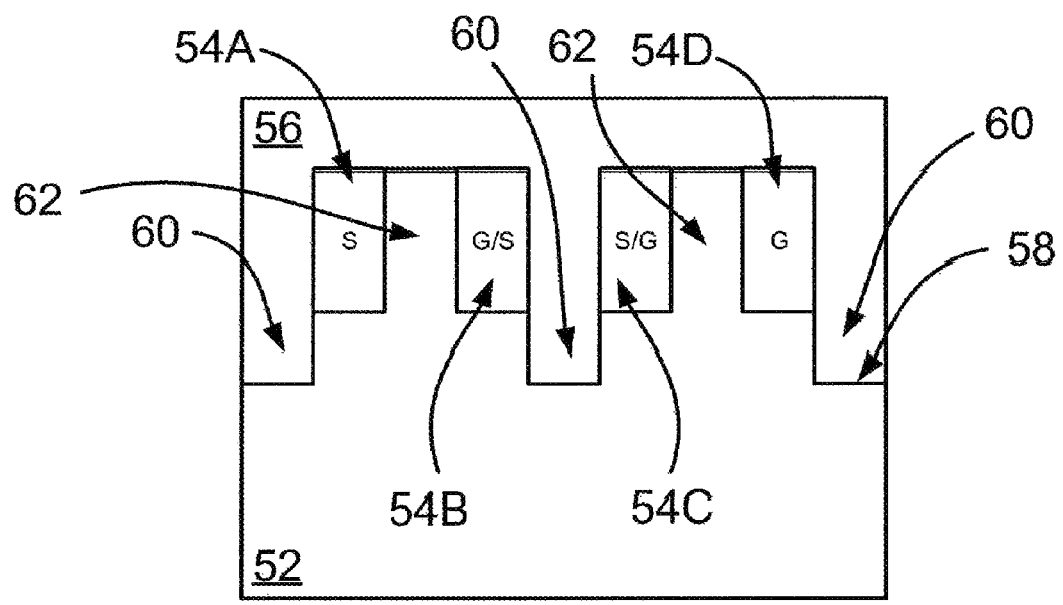
FIG. 8 shows a capacitive environmental sensor according to another embodiment of the proposed concept.

FIG. 8 shows a second embodiment of a capacitive environmental sensor. The sensor in FIG. 8 is similar in many respects to the sensor described above in relation to FIG. 7. The main difference between the sensor shown in FIG. 8 and the sensor described above in relation to FIG. 7 is that in some of the spaces between the electrodes 54 in FIG. 8, the surface 58 of the substrate 52 extends upwards to at least partially fill the space between the electrodes 54. For instance, the space between the electrodes 54A and 54B is substantially filled by an upwardly extending portion 62 of the substrate 52. Similarly, a portion 62 of the substrate 52 extends upwardly between the electrodes 54C and 54D. This arrangement has been found to reduce the sensitivity of the sensor to the presence of an interface layer to a greater extent than the example shown in FIG. 7, whilst returning sensitivity to the target substance.

FIG. 9 illustrates the results of simulations relating to a capacitive environmental sensor of the kind shown in FIG. 7, while FIG. 10 illustrates the results of similar simulations that have been carried out in relation to a sensor of the kind shown in FIG. 8. FIGS. 9 and 10 both illustrate that when arrangements of the kind shown in FIGS. 7 and 8 are used, sensitivity to the presence of an interface layer can be factored out while retaining sensitivity to a target substance. In these simulations, the target substance is assumed to be moisture (i.e. it is assumed that the sensor in this example is a humidity sensor) and the composition of the interface layer is assumed to comprise condensed water ($\varepsilon$=80). For simulation and demonstration purposes, the sensor layer is assumed to consist of polyimide with a nominal dielectric constant ($\varepsilon$) of 3, and showing typical variations of approximately +−20% over the full relative humidity range. Substrate permittivity is assumed to be 4.2, representing $SiO_2$.

The various plots and the scaling factors in FIGS. 9 and 10 are summarised below in Tables 4 and 5, respectively.

TABLE 4

Differential Measurements in FIG. 9.

| FIG. | Reference Numeral | Measurement |
|---|---|---|
| 9A; 9B | 70 | Single |
| 9A; 9B | 71 | Single - 1.0 * Double |
| 9A; 9B | 72 | Double |
| 9A; 9B | 73 | Single - 2.0 * Double |
| 9A; 9B | 74 | Single - 2.4 * Double |
| 9A; 9B | 75 | Single - 2.7 * Double |

TABLE 5

Measurements in FIG. 10.

| FIG. | Reference Numeral | Measurement |
|---|---|---|
| 10A; 10B | 80 | Single |
| 10A; 10B | 81 | Single - 1.0 * Double |
| 10A; 10B | 82 | Double |
| 10A; 10B | 83 | Single - 2.0 * Double |
| 10A; 10B | 84 | Single - 2.4 * Double |
| 10A; 10B | 85 | Single - 2.7 * Double |

Figures 9A, 9B:
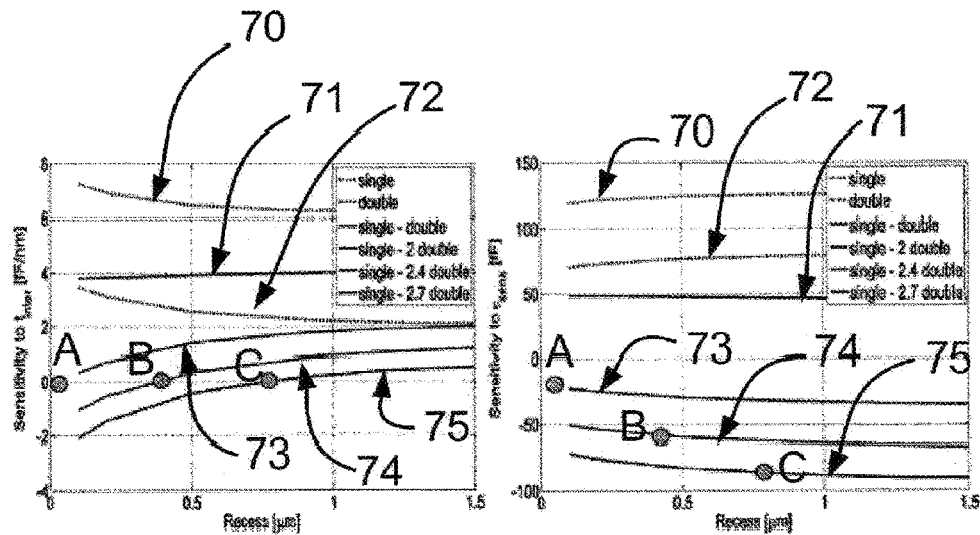
FIGS. 9A and 9B show the effect of varying the depth of the recesses in the embodiment of FIG. 7 on sensitivity of the sensor to the thickness of an interface layer.

In accordance with embodiments of the proposed concept, the depth of the recesses 60 can be selected along with the appropriate scaling factor so that the sensitivity of the sensor to a factor other than the presence of the target substance can be reduced or removed. The points A, B, C in FIGS. 9A and 9B represent three corresponding choices of recess depth and scaling factor. Taking the example of point B, the recess depth is approximately 0.4 µm and the scaling factor is selected to be 2.4 (see plot 74). FIG. 9A shows that these values, sensitivity to the interface layer is approximately zero.

Thus, to make a differential measurement, a first measurement can be made in the single spaced electrode configuration and then a second measurement can be made in the double spaced electrode configuration. The result of the measurement in the double spaced electrode configuration may then be multiplied by the scaling factor of 2.4 and deducted from the result in the single spaced electrode configuration. This result will not be sensitive to the interface layer as is clear from FIG. 9A. Turning to FIG. 9B, and referring to point B shown therein, which corresponds to the same recess depth (approximately 0.4 µm) and scaling factor (2.4), it can be seen that the sensor is still sensitive to the presence of the target substance.

Point C in FIGS. 9A and 9B is an alternative choice of parameters in which the recess depth is slightly greater (approximately 0.7 µm) and the scaling factor is 2.7. It can be seen that point C in FIG. 9B provides an even greater sensitivity to the presence of the target substance then point B, while reducing sensitivity to the interface layer.

Figures 10A, 10B:
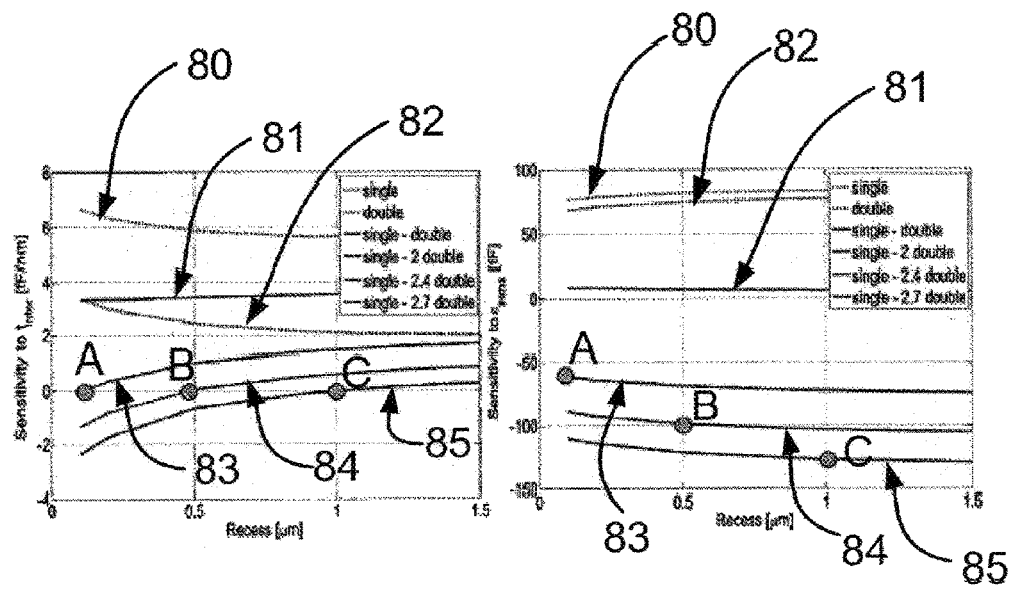
FIGS. 10A and 10B show the effect of varying the depth of the recesses in the embodiment of FIG. 8 on sensitivity of the sensor to the thickness of an interface layer.

FIGS. 10A and 10B show results that are similar to those described above in relation to FIGS. 9A and 9B except that they apply to the embodiment of FIG. 8. Each of points A, B and C in FIGS. 10A and 10B represent different choices of recess depth and respective scaling factors. As can be appreciated by comparison of FIGS. 9B and 10B, the embodiment of FIG. 8 can allow sensitivity to the interface layer to be reduced or removed by while retaining an enhanced sensitivity to the target substance compared to the embodiment of FIG. 7. For instance, the sensitivity of the sensor to the target substance at point B in FIG. 10B (recess depth=0.5 µm) is nearly double that of point B in FIG. 9B (recess depth=approximately 0.4 µm).

FIGS. 11 and 12 illustrate the results of simulations similar to those described above in relation to FIGS. 9 and 10, except that they demonstrate the reduction or removal of the sensitivity of the device to the permittivity of the substrate. The results in FIG. 11 correspond to a device of the kind described above in relation to FIG. 7, while the results in FIG. 12 correspond to a sensor of the kind described above in relation to FIG. 8.

Figures 11A, 11B:
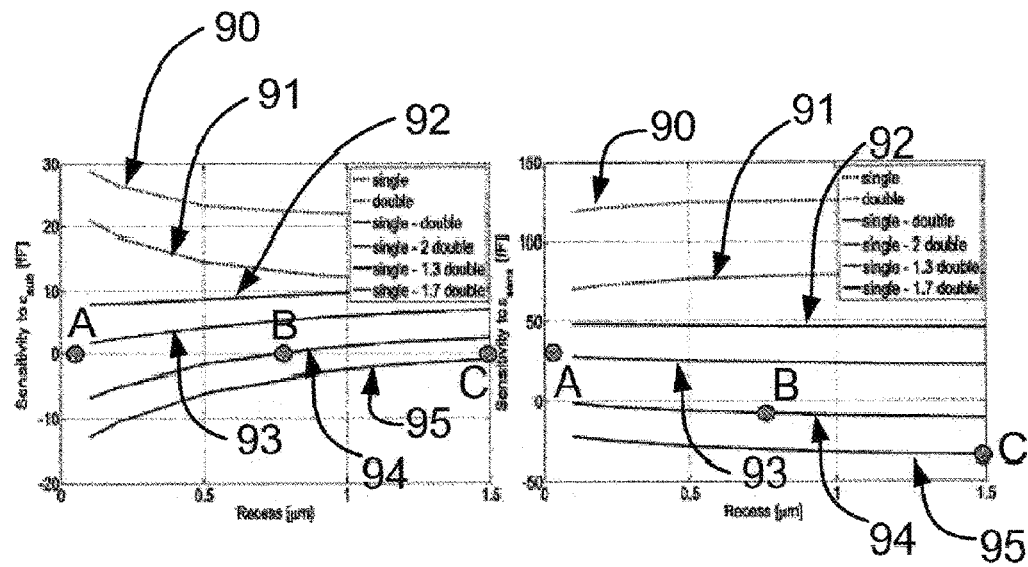
FIGS. 11A and 11B show the effect of varying the depth of the recesses in the embodiment of FIG. 7 on sensitivity of the sensor to changes in the permittivity of the substrate.

Table 6 summarises the various plots in FIGS. 11A and 11B and the scaling factors used.

TABLE 6

Measurements in FIG. 11.

| FIG. | Reference Numeral | Measurement |
|---|---|---|
| 11A; 11B | 90 | Single |
| 11A; 11B | 91 | Double |
| 11A; 11B | 92 | Single - 1.0 * Double |
| 11A; 11B | 93 | Single - 1.3 * Double |
| 11A; 11B | 94 | Single - 1.7 * Double |
| 11A; 11B | 95 | Single - 2.0 * Double |

Again, in FIG. 11A each of points A, B and C are chosen such that the sensitivity to the permittivity of the substrate is approximately zero. Turning to FIG. 11B, it can be seen that for each of points A, B and C (which correspond to the same recess depths and scaling factors used in the points A, B and C in FIG. 11A), the sensitivity of the sensor to the target substance is retained during the differential measurement. In FIG. 11B, it is noted that points A and C may be preferred to point B, since the retained sensitivity of the sensor to the target substance is substantially greater at points A and C than at point B. In any case, FIG. 11 demonstrates that, by appropriate selection of the depth of the recess and corresponding scaling factor, sensitivity of the sensor to the target substance can be retained while reducing or removing sensitivity of the sensor to the permittivity of the substrate.

Table 7 summarises the various plots in FIG. 12 and the scaling factors used.

TABLE 7

Measurements in FIG. 12.

| FIG. | Reference Numeral | Measurement |
| --- | --- | --- |
| 12A; 12B | 100 | Single |
| 12A; 12B | 101 | Single - 1.0 * Double |
| 12A; 12B | 102 | Single - 2.0 * Double |
| 12A; 12B | 103 | Double |
| 12A; 12B | 104 | Single - 3.0 * Double |
| 12A; 12B | 105 | Single - 4.0 * Double |

Figures 12A, 12B:
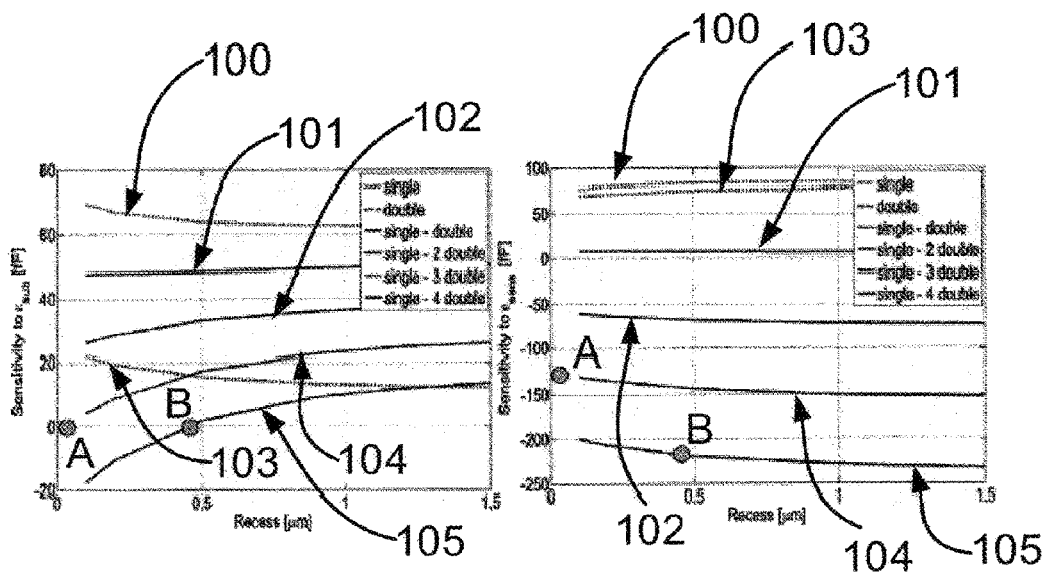
FIGS. 12A and 12B show the effect of varying the depth of the recesses in the embodiment of FIG. 8 on sensitivity of the sensor to changes in the permittivity of the substrate.

In FIG. 12A, two illustrative values of recess depth and their associated scaling factors are chosen (see points A (recess depth approximately 0.05 µm; scaling factor=3.0) and B (recess depth approximately 0.45 µm; scaling factor=4.0)). At both points A and B, the sensitivity of the sensor to the permittivity of the substrate is substantially removed.

Turning to FIG. 12B, it can be seen that at both points A and B, the sensitivity of the sensor to the target substance is retained. Comparison of FIG. 12B with FIG. 11B reveals that the sensitivity of the sensor in FIG. 8 compared to the sensitivity of the sensor in FIG. 7 to the target substance is somewhat larger in the case of sensor of FIG. 8. Again therefore, it is demonstrated that an arrangement in which the substrate, in a space separating at least one pair of electrodes, extends upwardly to at least partially fill the space, can further enhance the extent to which the sensitivity to the target substance can be retained while removing sensitivity to factors other than the target substance.

In the examples described above, only a single cause of potential drift in the output of a capacitive environmental sensor has been considered at a time. Thus, in the simulation results of FIGS. 9 and 10, the presence of an interface layer is considered while in the simulations of FIGS. 11 and 12, sensitivity of the sensor to the permittivity of the substrate is considered. It is envisaged that in some embodiments it may be possible to reduce or remove sensitivity to more than one factor other than the presence of the target substance. For example, in some examples, it may be possible to factor our both the permittivity of the substrate and the presence of an interface layer. An example of this will now be described with reference to FIGS. 13 and 14.

Figure 13:
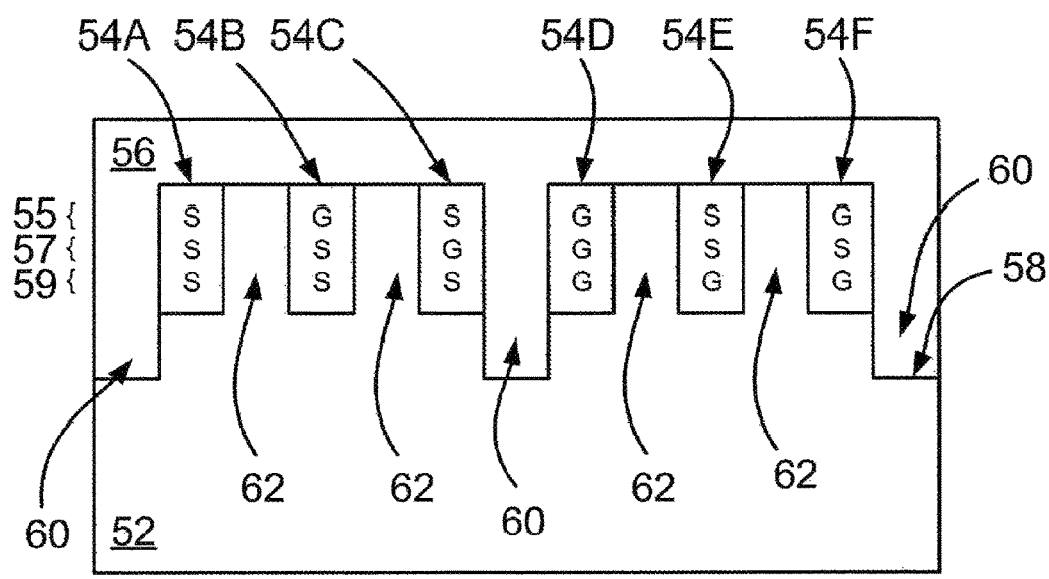
FIG. 13 shows a capacitive environmental sensor according to a further embodiment of the proposed concept.

In order to factor out, for example, two separate sensitivities other than the sensitivity to the presence of the target substance, a third electrical configuration can be used. FIG. 13 shows an example of a capacitive environmental sensor according to another embodiment of the proposed concept.

The sensor is similar in many respects to the sensors described above in relation to FIGS. 7 and 8 and like reference numerals have been used. The sensor shown in FIG. 13 differs from the examples of FIGS. 7 and 8 as follows.

The electrodes 54 in FIG. 13 are switchable between three different electrical configurations. These electrical configurations are shown in FIG. 13 using reference numerals 55, 57 and 59. The electrical configuration 55 is a single spaced configuration of the kind described above in which the electrodes 54A, 54B, 54C, 54D, 54E, 54F are connected either to a signal or to ground as follows "SGSGSG". The electrical configuration 57 shown in FIG. 13 is the double space configuration in which the electrodes are connected to signal or to ground as follows "SSGGSS". The third electrical configuration 59 shown in FIG. 13 is referred to herein as the "triple spaced configuration" or the "triple" configuration. In the triple spaced configuration the electrodes are connected to signal or ground as follows "SSSGGG". It is noted that while the single spaced configuration in principle requires a minimum of two electrodes and the double spaced configuration requires a minimum of four electrodes, a minimum of six electrodes are required to support the triple spaced configuration.

Note that in FIG. 13A, in common with the example of FIG. 8, some of the spaces include portions 62 of the substrate 52 that extend upwardly to fill the space.

Figures 14A, 14B, 14C:
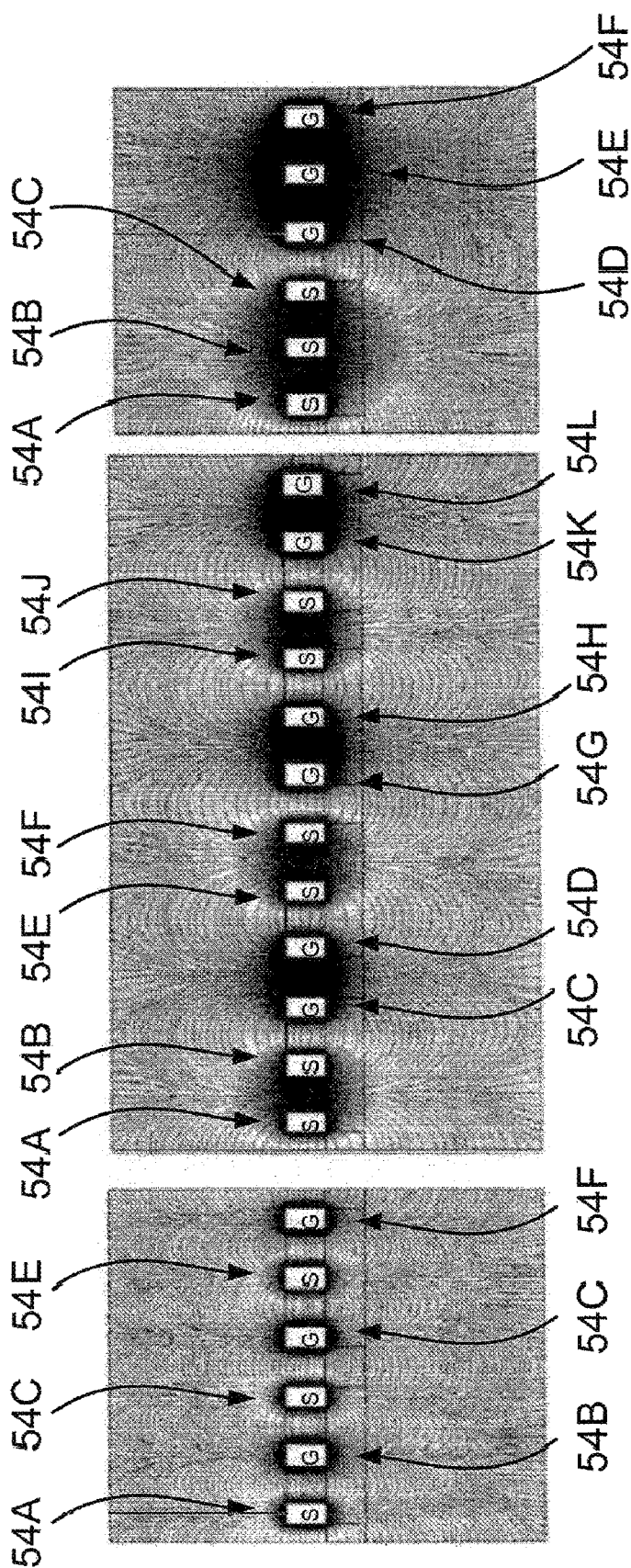
FIGS. 14A to 14C show the electrical field line distributions for various electrical configurations of the capacitive environmental sensor shown in FIG. 13.

The field lines produced by the single, double and triple spaced configurations described above in relation to FIG. 13 are shown in FIGS. 14A, 14B and 14C respectively.

In FIG. 13, the recesses 60 in a surface 58 of a substrate 52 are provided at every third electrode spacing in contrast to the examples described above in relation to FIGS. 7 and 8 in which the recesses 60 are provided in every second electrode spacing.

For each electrical configuration 55, 57, 59 shown in FIG. 13, the sensitivity of the sensor to an interface layer $\partial C/\partial t_{inter}$, the permittivity of the substrate $\partial C/\partial \varepsilon_{sub}$ and to the presence in the sensor layer 56 of the target substance $\partial C/\partial \varepsilon_{sens}$ can be simulated by calculating the electric field distribution and electrode capacitances, and represented in matrix format as follows:

$$\begin{bmatrix} \partial C_{single} \\ \partial C_{double} \\ \partial C_{triple} \end{bmatrix} = \begin{bmatrix} a & b & c \\ d & e & f \\ g & h & i \end{bmatrix} \begin{bmatrix} \partial \varepsilon_{sens} \\ \partial t_{inter} \\ \partial \varepsilon_{sub} \end{bmatrix}$$

$$= \begin{bmatrix} 62.77 & 6.65 & 84.38 \\ 40.28 & 3.37 & 50.85 \\ 49.65 & 2.24 & 18.04 \end{bmatrix} \begin{bmatrix} \partial \varepsilon_{sens} \\ \partial t_{inter} \\ \partial \varepsilon_{sub} \end{bmatrix}$$

Taking a linear combination of the three electrical configurations results in:

$$\begin{bmatrix} x_1 & x_2 & x_3 \end{bmatrix} \begin{bmatrix} \partial C_{single} \\ \partial C_{double} \\ \partial C_{triple} \end{bmatrix} =$$

$$(x_1 a + x_2 d + x_3 g)\partial \varepsilon_{sens} + (x_1 b + x_2 e + x_3 h)\partial t_{inter} + (x_1 c + x_2 f + x_3 i)\partial \varepsilon_{sub}$$

Solving for $(x_1 b + x_2 e + x_3 h) = 0$ and $(x_1 c + x_2 f + x_3 i) = 0$:

$$x_2 = \left\{ -\frac{b}{e} + \frac{h}{e}\left(c - \frac{bf}{e}\right)\left(\frac{e}{ie - hf}\right) \right\} x_1$$

$$x_3 = -\left(c - \frac{bf}{e}\right)\left(\frac{e}{ie - hf}\right)x_1$$

Choosing $x_1=1.0$, it is found that for $x_2=-1.4390$ and $x_3=-1.0164$, this combination of multiplication factors can cancel both drift effects (the interface layer and the permittivity of the substrate) while retaining a sensitivity toward the presence of the target substance in the sensor layer of 58.84fF. To boost the sensitivity of the sensor to the presence of the target substance, a value of $x_1$ greater than 1.0 may be chosen (the values of $x_2$ and $x_3$ would need to be scaled correspondingly). However, this kind of scaling can result in an increase in noise in the sensed value.

Differential measurements generally involve the subtraction of two or more signals, possibly with multiplication factors. During this process, the noise from the two or more signals is combined. For instance, suppose there are two signals with uncorrelated noise variance $\sigma_1^2$ and $\sigma_2^2$, then the differential signal $S_{diff}=S_1-XS_2$ (where X is the scaling factor) will a variance of $\sigma_1^2+X^2\sigma_2^2$. For large X, the noise associated with the differential signal can become significant.

Nevertheless, for capacitive sensors, drift is oftentimes a more significant issue than noise. Accordingly, it is recognised that using a sensor and corresponding method of the kind disclosed herein may afford the benefits in a significant improvement in signal accuracy due to reduced drift at a relatively modest cost in terms of increased noise.

Notwithstanding this, care should be taken when choosing the scaling factors used. For instance, consider a measurement in a single spaced electrode configuration as a linear superposition of mutually uncorrelated signal, drift and noise components:

Single=Signal$_{Single}$+Drift$_{Single}$+Noise$_{Single}$

Similarly for a measurement in a double spaced electrode configuration:

Double=Signal$_{Double}$+Drift$_{Double}$+Noise$_{Double}$

Because the two measurements are obtained in similar ways from the same electrode structure (assuming that they are switched between the two configurations between measurements), it may be assumed that the signal and drift components are fully correlated:

Signal$_{Double}=m_{Signal}$Signal$_{Single}$

Drift$_{Double}=m_{Drift}$Drift$_{Single}$ where $m_{Signal}$ and $m_{drift}$ are proportionality factors. Then construct a differential measurement as an over an angle $\theta$ rotation in the Cartesian Single-Double coordinate system:

Differential=cos($\theta$)Single+sin($\theta$)Double where:

Signal$_{Differential}$=cos($\theta$)Signal$_{Single}$+sin($\theta$)Signal$_{Double}$ Drift$_{Differential}$=cos($\theta$)Drift$_{Single}$+sin($\theta$)Drift$_{Double}$ Noise$_{Differential}$=cos($\theta$)Noise$_{Single}$+sin($\theta$Noise$_{Double}$ This can be rewritten as:

Differential=Signal$_{Differential}$+Drift$_{Differential}$+Noise$_{Differential}$ In a typical sensor, measurements in a single space or double spaced electrical configuration have uncorrelated noise with equal variances, as they are measured independently by the same circuit. Thus:

$\sigma_{Double}=\sigma_{Single}$ where $\alpha_{Single}^2$ and $\sigma_{Double}^2$ are the variances of Noise$_{Single}$ and Noise$_{double}$, respectively. Consequently, the variance of Noise$_{Differential}$ in constant as a function of $\theta$:

$\sigma_{Differential}^2=\sigma_{Single}^2\cos^2(\theta)+\sigma_{Double}^2\sin^2(\theta)=\sigma_{Single}^2$ Next, choosing $\theta$ such that Drift$_{Differential}=0$, which is true for $\tan(\theta_{optimal})=-\arctan(1/m_{Drift})$ it is noted that there are two possible solutions, namely:

$$\theta_{Optimal} = -\arctan\left(\frac{1}{m_{Drift}}\right) + k\pi, \text{ where } k = 0, 1$$

Consequently:

$$\text{Signal}_{Differential} = \cos(\theta_{optimal})\text{Signal}_{Single} + \sin(\theta_{optimal})\text{Signal}_{Double}$$

$$= \text{Signal}_{Single}\left(1 - \frac{m_{Signal}}{m_{Drift}}\right)\cos(\theta_{Optimal})$$

For comparing single a differential measurements k can be chosen such that the sign of Signal$_{Differential}$ is equal to that of Signal$_{Single}$. For this k:

$$\text{Signal}_{Differential} = \text{Signal}_{Single}\left|1 - \frac{m_{Signal}}{m_{Drift}}\right|\frac{1}{\sqrt{1 + \frac{1}{m_{Drift}^2}}}$$

$$= \text{Signal}_{Single}\frac{|m_{Drift} - m_{Signal}|}{\sqrt{m_{Drift}^2 + 1}}$$

In practice $\theta_{Optimal}$ can be chosen using a test or calibration system. Testing and calibration may be performed for each sensor individually. Alternatively, a representative sample of sensors may be used to derive parameters for use across a larger batch. The values can be stored in the sensor (e.g. in a reference table accessible by a microcontroller). These calibration values can also be stored across a range of operating conditions (e.g. different temperatures, pressures and so on) and used accordingly to the environment in which the sensor is located.

The examples set out above relate to differential measurements in which two measurements or three measurements are made. It is envisaged that in general this can be extended to an K-measurement approach, with arbitrarily large K.

It is also envisaged that the number of measurements made may more than strictly required to compensate for factors other than the sensitivity of the sensor to the target substance. Even where only a relatively small number of factors other than the sensitivity of the sensor to the presence of the target substance are to be compensated for, a relatively large number of capacitive measurements may be made in a plurality of respective electrical configurations of the electrodes. For instance, three or more capacitive measurements may be made in respective electrical configurations of the electrodes for accounting for a single factor such as the presence of an interface layer or changing permittivity of the substrate. In another example, four or more capacitive measurements may be made in respective electrical configurations of the electrodes for compensating for two factors such as the presence of an interface layer or changing permittivity of the substrate. By making more measurements than the number of factors to be removed, an over-determined set of equations can be formed. The solution of such an over-determined set of equations may typically be more stable (less noisy) than those described above.

If the elements of a K-dimensional vector x are different measurements taken with at least M different electrode configurations, with M smaller than or equal to K, then we can calculate a corrected N-dimensional vector y=Ax of corrected values with N smaller than or equal to M, where A is a N-by-K matrix of weight factors (N rows and K columns). The optimal matrix A can be found as follows.

Assume that the elements of y represent the actual values of the parameters to be determined (e.g. humidity, $CO_2$ concentration, etc.). Then assume that the k-th measurement x(k), taken with a k-th electrical configuration of the electrodes, is equal to b(k)y+r(k), where the first term is an ideal model response (in the absence of noise and other disturbing processes) and the second term is a disturb in the k-th measurement. The entire set of measurements, represented by the vector x, then can be written as x=Cy+r, where the matrix element of C in the k-th row and n-th column is equal to the n-th element of the vector b(k). In the ideal case, i.e. without the influence of factors other than the sensitivity of the sensor to the target substance, x would be equal to Cy, i.e., it would be a weighed sum of basis vectors c(n) (the columns of the model response matrix C), with the elements of y as weight factors. So any ideal model measurement should lie in the N-dimensional space spanned by the basis vectors c(k). Therefore the disturb vector r may be regarded as being orthogonal to that space, i.e. the inner product (c(n),r) of r with c(n) should be zero for all n. In that case (c(n),x)=(c(n),Cy) for all n. This can be written as $C^T x = C^T Cy$ (because it may be assumed that $C^T r=0$), where the matrix $C^T$ is the transpose of the matrix C. Provided that the vectors c(n) are mutually independent the n-by-n matrix $C^T C$ can be inverted, and $y=(C^T C)^{-1} C^T x = Ax$, where the matrix $A=(C^T C)^{-1} C^T$ is known as the pseudoinverse of matrix C.

The required model matrix C can be calculated, determined experimentally with a (typically large) set of calibration measurements under controlled environmental conditions (i.e. known vectors y), or a combination of both. C can also be made dependent on the history of the sensor (e.g. its age, or the ensemble of gasses it has previously detected) to accommodate for aging and/or degradation of the sensor (of course this requires an aging/degradation model). The matrix C may also be initially fixed when the sensor is sold, and later be updated to a better version, or updated to a more advanced matrix that includes an aging/degradation model. This approach can be used to improve the quality of already sold products with in-system updates, which is a frequently used approach for modern devices, especially for portable devices like mobile phones.

Embodiments of the proposed concept can be used in applications that required the sensing of substances such as moisture, gases such as $CO_2$ or volatile organic compounds. It is envisaged that a sensor of the kind described herein may be incorporated into a radio frequency identification (RFID) tag to support applications of this kind. It is further envisaged that a sensor of the kind described herein may be used in a smart building or in devices such as a mobile telephone or table. The smart building may be a greenhouse.

Accordingly, there has been described a capacitive environmental sensor and a method for determining the presence of a target substance (e.g. water) using differential capacitive measurements. The sensor includes a semiconductor substrate having a surface. The sensor also includes a plurality of sensor electrodes located on the surface. The electrodes are laterally separated on the surface by intervening spaces. The sensor further includes a sensor layer covering the electrodes. The sensor layer has a permittivity that is sensitive to the presence of the target substance. The surface of the substrate, in a space separating at least one pair of electrodes, includes a recess. The surface of the substrate, in a space separating at least one pair of electrodes, does not include a recess. The sensor may be provided in a Radio Frequency Identification (RFID) tag. The sensor may be provided in a smart building.

Although particular embodiments of the proposed concept have been described, it will be appreciated that many modifications/additions and/or substitutions may be made within the scope of the claimed concept.

The invention claimed is:

1. A capacitive environmental sensor comprising:
a semiconductor substrate having a surface;
a plurality of sensor electrodes located on the surface, wherein each pair of neighbouring electrodes are laterally separated on the surface by a respective intervening space; and
a sensor layer covering the electrodes, wherein the sensor layer has a permittivity that is sensitive to the presence of a target substance;
wherein the surface of the substrate, in a space separating at least one pair of electrodes, includes a recess, wherein the surface of the substrate, in a space separating at least one other pair of electrodes, does not include a recess;
and wherein either:
the electrodes include a plurality of separate groups of electrodes arranged on the substrate, each group having a different electrical configuration, for making differential capacitive measurements between each group; or
the electrodes are switchable between a plurality of different electrical configurations for making differential capacitive measurements.

2. The capacitive environmental sensor according to claim 1, wherein the spaces in which the surface of the substrate includes a recess alternate in a periodic sequence with the spaces in which the surface of the substrate does not include a recess.

3. The capacitive environmental sensor according to claim 2, wherein the substrate, in at least one space separating a pair of electrodes that does not include a recess, extends upwards to at least partially fill the space.

4. The capacitive environmental sensor according to claim 3, wherein the periodic sequence is of the form 'XZXZX', where 'X' denotes a space that includes a recess and where 'Z' denotes a space in which the substrate extends upwards to at least partially fill the space.

5. The capacitive environmental sensor according to claim 3, wherein the periodic sequence is of the form 'XZZXZZX', where 'X' denotes a space that includes a recess and where 'Z' denotes a space that does not include a recess.

6. The capacitive environmental sensor according to claim 2, wherein the periodic sequence is of the form 'XYXYX', where 'X' denotes a space that includes a recess and where 'Y' denotes a space that does not include a recess.

7. The capacitive environmental sensor according to claim 1, operable to make a differential capacitive measurement to determine the presence of the target substance by:

making a first measurement of capacitance of at least some of the electrodes in a first electrical configuration;

making a second measurement of capacitance of at least some of the electrodes in a second electrical configuration;

applying a scaling factor to the second measurement to compensate for sensitivity of the sensor to a factor other than the presence of the target substance; and determining the presence of the target substance by evaluating the difference between the first measurement and the second measurement.

8. The capacitive environmental sensor of claim 7, wherein making the differential capacitive measurement further includes:

making a third measurement of capacitance of at least some of the electrodes in a third electrical configuration;

applying a scaling factor to the third measurement to compensate for sensitivity of the sensor to a factor other than the presence of the target substance, and determining the presence of the target substance by evaluating the differences between the first, second and third measurements.

9. The capacitive environmental sensor according to claim 1, operable to make a differential capacitive measurement to determine the presence of the target substance by:

making a plurality of measurements of capacitance of at least some of the electrodes in respective, different, electrode configurations;

applying a scaling factor to at least some of the measurements to compensate for sensitivity of the sensor to factors other than the presence of the target substance, and determining the presence of the target substance by evaluating the differences between the measurements, wherein the number of measurements of capacitance made is at least two more than the number of factors other than the presence of the target substance compensated.

10. The capacitive environmental sensor according to claim 1, wherein the substrate includes a plurality of layers, and wherein the sensor electrodes are located on a surface of one of the plurality of layers.

11. The capacitive environmental sensor of claim 1, wherein the target substance comprises water, $CO_2$ or a volatile organic compound (VOC).

12. A smart building including the capacitive environmental sensor claim 1.

13. A method for determining the presence of a target substance using differential capacitive measurements, the method comprising:

providing a capacitive environmental sensor according to claim 1;

making a first measurement of capacitance of at least some of the electrodes in a first electrical configuration;

making a second measurement of capacitance of at least some of the electrodes in a second electrical configuration;

applying a scaling factor to the second measurement to compensate for sensitivity of the sensor to a factor other than the presence of the target substance; and determining the presence of the target substance by evaluating the difference between the first measurement and the second measurement.

14. A capacitive environmental sensor comprising:

a semiconductor substrate having a surface;

a plurality of sensor electrodes located on the surface in a single level of electrodes, wherein each pair of neighbouring electrodes are laterally separated on the surface by a respective intervening space; and a sensor layer covering the electrodes, wherein the sensor layer has a permittivity that is sensitive to the presence of a target substance;

wherein the surface of the substrate, in the respective intervening space separating at least one pair of electrodes, includes a recess, wherein the surface of the substrate, in the space separating at least one other pair of electrodes, does not include a recess;

and wherein either:

the electrodes include a plurality of separate groups of electrodes arranged on the substrate, each group having a different electrical configuration, for making differential capacitive measurements between each group; or the electrodes are switchable between a plurality of different electrical configurations for making differential capacitive measurements.

* * * * *